US006381015B1

(12) United States Patent
Sonehara et al.

(10) Patent No.: US 6,381,015 B1
(45) Date of Patent: Apr. 30, 2002

(54) INSPECTION APPARATUS USING OPTICAL INTERFEROMETER

(75) Inventors: Tsuyoshi Sonehara, Kokubunji; Yuji Miyahara, Kodaira; Masao Suga, Hachioji, all of (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/380,268
(22) PCT Filed: May 26, 1997
(86) PCT No.: PCT/JP97/01755
§ 371 Date: Aug. 27, 1999
§ 102(e) Date: Aug. 27, 1999
(87) PCT Pub. No.: WO98/53733
PCT Pub. Date: Dec. 3, 1998

(51) Int. Cl.[7] .................................................. G01B 9/02
(52) U.S. Cl. ........................................ 356/357; 356/450
(58) Field of Search ........................... 356/450, 479, 356/497

(56) References Cited

U.S. PATENT DOCUMENTS 5,610,714 A * 3/1997 Malvern et al. ............ 356/350
5,905,572 A * 5/1999 Li .............................. 356/345

FOREIGN PATENT DOCUMENTS

JP          4-310847    11/1992
JP          7-55702     3/1995

OTHER PUBLICATIONS

Spie vol. 1889, "Optical Characterization of Dense Tissues Using Low–Coherence Interferometry", J. Schmitt et al, pp. 197–211.

Optics Letters, vol. 21, No. 22, Nov. 15, 1996, "Self–phase-–modulated Kerr–lens mode–locked Cr:forsterite laser source for optical coherence tomography", B. Bouma et al, pp. 1839–1841.

The 57th Autumn Meeting, 1996, The Japan Society of Applied Physics, 8p–B–5, 'M. Haruna et al.

* cited by examiner

Primary Examiner—Frank G. Font
Assistant Examiner—Andrew H. Lee
(74) Attorney, Agent, or Firm—Mattingly, Stanger & Malur, P.C.

(57) ABSTRACT

According to an aspect of the present invention, there is provided an inspection apparatus using an optical interferometer including splitting and combining means (3) for splitting light from a light source (1) into incident light (41) irradiated on a sample and reference light (40) and combining signal light which is light scattered or reflected by the sample (7, 42) and the reference light, a modulator (4, 5, 10) for subjecting the reference light to phase modulation and a photo detector (9) for detecting light combined by the splitting and combining means (3), the inspection apparatus further including first detecting means (12-1) for detecting amplitudes of first signal components having frequencies of multiples of odd numbers of a fundamental modulation frequency of the modulator in a signal from the photo detector (9), second detecting means (12-2) for separating and detecting amplitudes of second signal components having frequencies of multiples of even numbers of the fundamental modulation frequency in the signal from the photo detector and means (14) for calculating an intensity of the signal light by using the amplitudes of the first and the second signal components for providing high signal stability and signal-to-noise ratio and in measuring a sample of a biomedical tissue or the like having large scattering or attenuation of light, distributions of a refractive index and an extinction coefficient up to a portion having a large depth can be measured with high accuracy.

17 Claims, 10 Drawing Sheets

INSPECTION APPARATUS USING OPTICAL INTERFEROMETER

BACKGROUND OF THE INVENTION

1. Field of the Invention

The present invention relates to an inspection apparatus using an optical interferometer for inspecting information concerning distribution of optical constant of a sample such as refractive index, extinction coefficient or the like as well as geometrical size of a sample or the like by laying a sample of a biomedical tissue or the like under exposure of light and detecting light scattered or reflected by the sample by using an optical interferometer.

2. Description of the Related Art

As examples of report of apparatus with an object of measurement concerning optical property or geometrical size of a sample by laying a sample of a biomedical tissue or the like under exposure of low coherent light and detecting light scattered or reflected by the sample, there are SPIE, Vol. 1889, 1993, pp. 197–211 (Literature 1), OPTICS LETTERS, Vol. 21, 1996, pp. 1839–1841 (Literature 2) and Proceedings of No. 57 Applied Physics Society, No. 0 separate volume, p.1213 (Literature 3).

According to Literature 1, light scattered or reflected by a sample is detected by using an optical interferometer for splitting light from a super luminescent diode (SLD) and modulating respective split light by respectively different frequency by an acousto-optic modulator. The acousto-optic modulator can provide pure frequency shift to light, a processing of a signal detected by the optical interferometer is carried out by narrow-band reception by a single frequency or lock-in detection in synchronism with a beat signal and the signal processing is comparatively simple. However, there are caused drawbacks in which a constitution of an optical system is complicated and large-sized, alignment of the optical system is troublesome and measurement of a sample by multi-wavelength light is troublesome and so on.

According to Literature 2 and Literature 3, light scattered or reflected by a sample is detected by using an optical interferometer for modulating reference light by using PZT (piezoelectric vibrator) as a phase modulator. According to Literature 2, an output from the interferometer is made to pass through a band-pass filter, and subjected to envelope detection, successively, sampling by an A-D converter is executed. According to Literature 3, an output from the optical interferometer is made to pass a single mode optical fiber, interfered light is filtered, only reflected straight moving light is detected by a photodiode, thereafter, the light is made to pass a high-pass filter and sampling by an A-D converter is executed. According to modulation of reference light by using PZT, a constitution of an apparatus is comparatively small-sized, alignment of an optical system is facilitated and expansion to measurement of a sample by multi-wavelength light is not so difficult.

SUMMARY OF THE INVENTION

According to modulation of reference light using PZT as a phase modulator in the above-described conventional technology, optical-paths of side band wave and carrier wave are the same and the side band wave and the carrier wave cannot be separated from each other and accordingly, there poses a problem in which pure frequency shift cannot be provided continuously to the reference light, some phase modulation is provided to the reference light and a stable signal cannot be detected by only receiving by the narrow-band reception in a single frequency, an output signal from a photo detector detected by the optical interferometer.

The conventional technology using envelope detection and a high-pass filter cannot be regarded as a technology sufficient for achieving detection of a stable signal, compared with narrow-band reception in a single frequency or lock-in detection in synchronism with a modulated signal, reception band of a signal is far wide (for example, a receiving band width of a signal is wide by 1000 times or more in comparison with lock-in detection with time constant of 1 sec when frequency is 1 KHz) and therefore, one cannot make full use of the characteristic for executing detection of light with high-sensitivity by using the optical interferometer (in principle, detection of single photon is feasible) and there cannot be achieved a signal-to-noise ratio near to its theoretical limit (when notation h designates Plank's constant, notation B designates band width of detecting system, notation P designates power of signal light and notation v designates frequency of light, signal-to-noise ratio=S/N=P/(hvB) and the S/N may be referred to as quantum noise limit).

It is an object of the present invention to provide an inspection apparatus using an optical interferometer for executing optical detection by an optical interferometer using a general optical modulator providing phase modulation such as PZT, an electro-optic modulator or the like to thereby simultaneously enable stable signal detection and narrow-band reception of signal in order to execute high-sensitivity detection of light using the optical interferometer by a signal-to-noise ratio near to its theoretical limit.

According to an inspection apparatus using an optical interferometer of the present invention, incident light is made to be irradiated on a predetermined point of a sample and light scattered or reflected by the sample is detected as signal light by an optical interferometer, when a fundamental frequency of phase modulation provided to 1 or 2 or 3 of the reference light, the incident light and the signal light is set to f, in an output signal from a photo detector, since one of first signal components having frequencies of multiples of odd numbers of the fundamental frequency f of the phase modulation and at least one of second signal components having frequencies of multiples of even numbers of the fundamental frequency f of the phase modulation are detected and relative intensity of the signal light is calculated from the amplitudes of the first and the second signal components.

According to a blood glucose level monitoring apparatus of the present invention for monitoring a blood glucose level in a biomedical tissue by detecting a glucose concentration in the biomedical tissue, there are provided an optical interferometer including a light source for emitting light having a predetermined wavelength absorbed by glucose in a visible, near infrared, infrared (500 nm through 2000 nm) range, splitting and combining means for splitting light from the light source into incident light irradiated on the biomedical tissue and reference light and combining signal light which is light scattered or reflected by the biomedical tissue and the reference light, a modulator for subjecting the signal light to phase modulation, and a photo detector for detecting light combined by the splitting and combining means, further including first detecting means for detecting an amplitude $V_1$ of a first signal component having a frequency of a multiple of one of the fundamental modulation frequency of the modulator, second detecting means for separating and detecting an amplitude $V_2$ of a second signal component having a frequency of a multiple of two of the fundamental modulation frequency of the modulator in a signal from the photo detector and means for calculating an intensity of the signal light V* by the following equation $$V^* = \frac{1}{2}\sqrt{\frac{V_1^2}{J_1^2(\theta)} + \frac{V_2^2}{J_2^2(\theta)}}$$

where $J_1$ and $J_2$ designate Bessel functions and $\theta$ designates an amplitude of phase modulation of the signal light, by using the amplitudes of the first and the second signal components, in which the glucose concentration is detected by calculating an optical-path length between a plurality of interfaces of the tissue in the biomedical tissue and attenuation of light between the plurality of interfaces. Further, according to the blood glucose level monitoring apparatus of the present invention, the amplitude $V_1$ of the first signal component and the amplitude $V_2$ of the second signal component are calculated by subjecting the signal from the photo detector to Fourier transformation by a Fourier transform device.

DETAILED DESCRIPTION OF THE PREFERRED EMBODIMENT

A detailed explanation will be given of the present invention in reference to the attached drawings as follows.

(First Embodiment)

Figure 1:
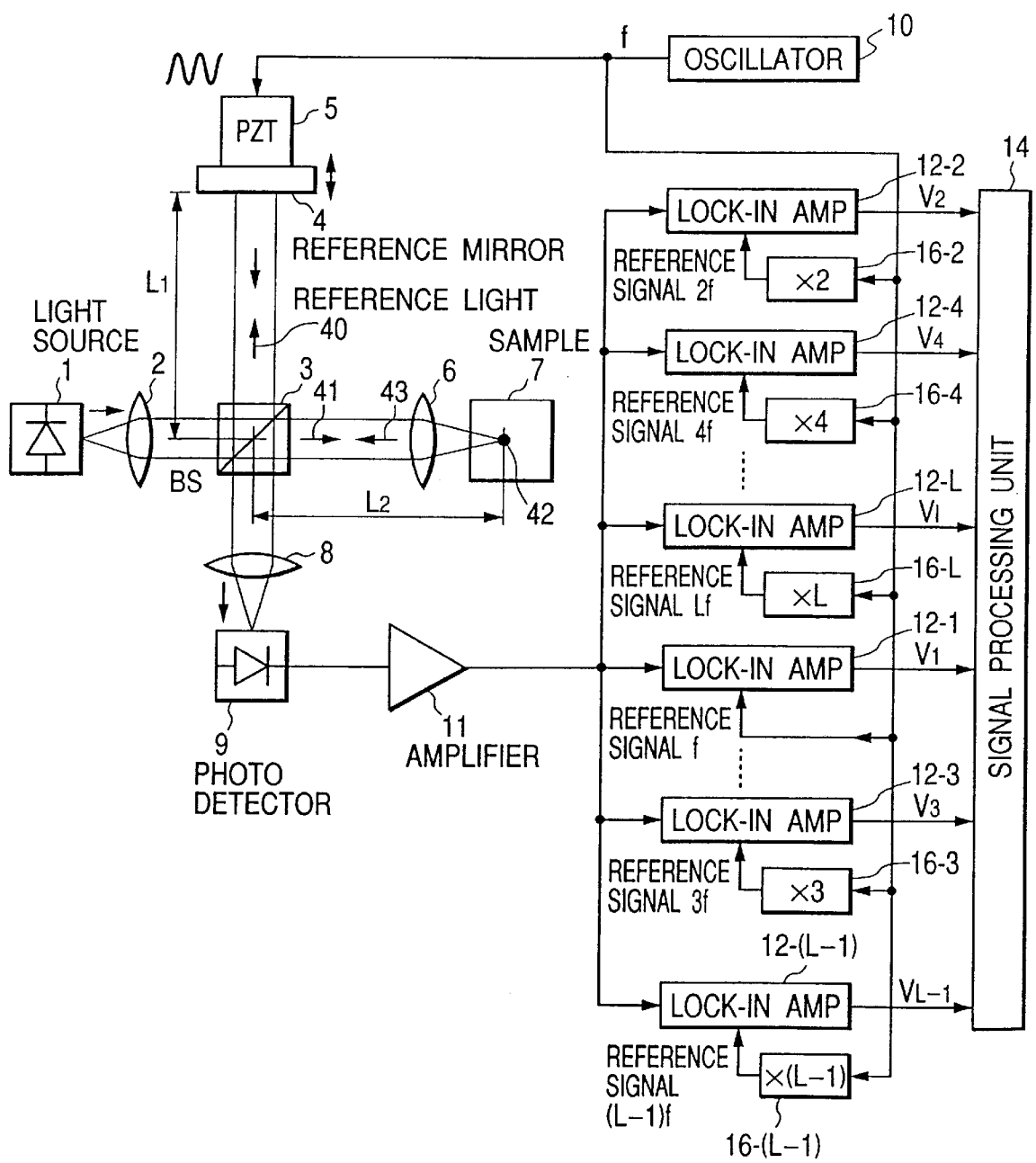
FIG. 1 is a diagram showing a constitution of an inspection apparatus using an optical interferometer according to a first embodiment of the present invention.

FIG. 1 is a diagram showing a constitution of an inspection apparatus using an optical interferometer according to a first embodiment of the present invention. According to the embodiment, there is used a Michelson interferometer which is widely known. As a light source 1, a super luminescent diode (SLD) having a wavelength of $\lambda=840$ nm and a coherent length of $L_c=35$ $\mu$m is used and as a photo detector 9, a semiconductor photodiode is used. Light from the light source 1 is collimated by a lens 2 and is divided (split) into two beams of reference light 40 and incident light 41 for exposing a sample 7 thereunder by a beam splitter 3. As examples of the sample 7, which can be inspected by the apparatus of the embodiment, there are a multi-layer sample having different refractive indices, a sample suspended with particles, a biomedical tissue and so on, for example, there can be known information at an inner portion of a sample such as a spatial distribution of a refractive index or the like, a shape of a boundary face where an optical constant (refractive index or the like) at an inner portion of a sample is discontinuously changed.

The incident light 41 is focused to a predetermined point 42 in the sample 7 by a lens 6. The reference light 40 which is reflected orthogonally by a reference mirror 4 attached to PZT5 driven by an oscillator 10 and light which is the incident light 41 back scattered at the predetermined point 42 in the sample 7 (signal light 43) are combined at the beam splitter 3. Combined light produced by superposing the reference light 40 and the light back scattered at the predetermined point 42, is focused by a lens 8 and is detected by the photo detector 9. Output current from the photo detector 9 is converted into a voltage signal by a current input amplifier (amplifier) 11. An output signal from the amplifier 11 is fed into a plurality of lock-in amps 12-1, 12-2, ..., 12-L in parallel. An output signal from the oscillator 10 is fed into PZT5 in which an optical-path length $L_1$ is modulated in accordance with time t with w as angular frequency of modulation in a form shown below (Equation 3). Reference signals having frequencies of different multiples of modulation frequencies are inputted to respectives of the plurality of lock-in amps 12-1, 12-2, ..., 12-L, among output signals from the photo detector 9, at least one of first signal components having first frequencies of multiples of odd numbers of a fundamental frequency f of phase modulation and at least one of second signal components having second frequencies of multiples of even numbers of the fundamental frequency f of phase modulation are detected and an intensity of signal light is calculated by a signal processing unit 14 by using respective amplitudes of the detected first and the second signal components.

Only when a condition of Equation (1) is satisfied between an optical-path length $L_1$ from a split point of the beam splitter 3 of light from the light source 1 to the reference mirror 4 and an optical-path length $L_2$ from the split point to the predetermined (scatter) point 42 in the sample 7, interference is caused excellently between the reference light and the signal light (light where the incident light 41 is back scattered at the predetermined point 42 in the sample 7) on a photoelectric face of the photo detector 9 and a sufficiently large interference signal is provided. In Equation (1), notation $L_c$ designates a coherence length of the light source 1. In this case, the coherence length $L_c$ is $$L_c = \log_e 2 \cdot \frac{2}{\pi} \cdot \frac{\lambda^2}{\Delta\lambda}$$

where λ designates a wavelength of oscillated light from the super luminescent diode (SLD) and Δλ designates a full width at half maximum of spectra of the oscillated light from SLD or $L_c$ is a full width at half maximum of an intensity distribution when an intensity distribution of an interference signal is regarded as a function of the left hand side ($L_1-L_2$) of Equation (1) when a sample is constituted by a plane mirror placed orthogonally to the incident light.

$$|L_1-L_2| \leq L_c \quad (1)$$

When the condition of Equation (1) is sufficiently satisfied, a temporal change V(t) of the output signal from the amplifier 11 is expressed in the form of Equation (2).

$$V(t)=V_{DC}+V^* \cos\{2k(L_1-L_2)\} \quad (2)$$

where k=2π/λ (λ; wavelength of incident light), term $V_{DC}$ designates a direct current component which is not changed by interference between the reference light and the signal light and when the sample is in a range satisfying Equation (1), V* is proportional to a reflectivity of a boundary or a back scattering coefficient by scattering particles and V* is an amplitude of the output signal from the amplifier 11. PZT5 is inputted with an output signal from the oscillator 10 and the optical-path length $L_1$ is modulated in the form of Equation (3) in accordance with time t with notation A as an amplitude of the output signal from the oscillator 10 applied to PZT5 and ω as angular frequency of modulation.

$$L_1(t)=L_0+A \sin \omega t \quad (3)$$

When Equation (3) is substituted for Equation (2) and putting $L_0-L_2=\Delta L$, Equation (4) is obtained. In Equation (4), notation $J_n$ designates Bessel function of n-th order and summation Σ is carried out in respect of n=1, 2, ..., ∞.

$$\begin{aligned}V(t) &= V_{DC} + V^*\cos\{2k(\Delta L + A\sin\omega t)\} \\ &= V_{DC} + V^*\cos(2k\Delta L)J_0(2kA) + \\ &\quad 2V^*\cos(2k\Delta L)\sum J_{2n}(2kA) \times \cos(2n\omega t) - \\ &\quad 2V^*\sin(2k\Delta L)\sum J_{2n-1}(2kA) \times \sin\{(2n-1)\omega t\}\end{aligned} \quad (4)$$

Accordingly, amplitude $V_{2n}$ of a signal component of angular frequency Nω {N=2n (n is any of 1, 2, ...): even number} of the output signal from the amplifier 11 is expressed by Equation (5) and amplitude $V_{2m-1}$ of a signal component of angular frequency Mω {M=2m-1 (m is any of 1, 2, ...: odd number} is expressed by Equation (6).

$$V_{2n}=2V^*J_{2n}(2kA)\cos(2k\Delta L) \quad (5)$$

$$V_{2m-1}=2V^*J_{2m-1}(2kA)\sin(2k\Delta L) \quad (6)$$

In the meantime, although $\Delta L = L_{0-L2}$ is the constant term of the optical-path difference of the optical interferometer, it is very difficult to reduce the stability of the value of the optical-path difference ΔL sufficiently relative to the wavelength λ. According to measurement using a low coherent light source, the optical-path difference is changed by a mechanical method and accordingly, there is a change in temperature, backlash or the like of a stage or the like and considering even a change in a dimension of a sample, it is practically impossible to maintain the stability of the value of the optical-path difference sufficiently small in comparison with the wavelength λ. That is, when a variation with time of the optical-path difference ΔL is expressed by ΔL(t)=ΔL*+δ(t) (ΔL* is a time-average value of ΔL(t) and is a term which is not varied with time), it is difficult to establish δ(t)<<λ. For example, when the wavelength of the light source is set to λ=840 nm=0.00084 mm, δ(t) needs to be δ(t)<<0.00084 mm, it is very difficult to maintain $L_2$ constant, that is, to maintain the predetermined point in the sample constant in an order of the wavelength λ owing to presence of temperature distribution of constituent parts of a sample holding base, temperature change of an atmosphere, temperature change of the inner portion of the sample and so on, particularly in the case of a biomedical tissue, owing to body motion.

That is, ΔL(t) is varied with time and accordingly, Equation (4) receives modulation by the variation with time of ΔL(t) other than the modulation by Equation (3) and values of cos{2kΔL(t)} and sin{2kΔL(t)} in Equation (5) and Equation (6) may be varied significantly in a range of (+1 through -1) in measurement. Since $$2k\Delta L(t) = \frac{4\pi\Delta L(t)}{\lambda} = \frac{4\pi\Delta L^*(t)}{\lambda} + \frac{4\pi\delta(t)}{\lambda}$$

and therefore, when δ(t) is varied with time bet n δ(t)=0 to δ(t)=λ/2, values of cos{2kΔL(t)} and sin{2k ΔL(t)} is varied significantly in a range of (+1 through -1) in measurement. When δ(t) is changed while satisfying δ(t)≧λ, the values of cos{2kΔL(t)} and sin{2kΔL(t)} are varied significantly in the total range of (+1 through -1).

Accordingly, when the output signal from the amplifier 11 is inputted to a narrow-band receiver or a lock-in amp and only a specific one amplitude in the amplitudes $V_{2n}$ of the signal components of the angular frequency Nω {N=2n (n is any of 1, 2, ... ): even number} of the output signal from the amplifier 11 and the amplitudes $V_{2m-1}$ of the signal components of the angular frequency Mω {M=2m-1 (m is any of 1, 2, ... ): odd number}, is measured, a detected signal fluctuates significantly by changes of sin{2kΔL(t)} and cos{2kΔL(t)} and the amplitude of the specific signal component is varied in the form of sin{2kΔL*+2kδ(t)} and cos{2kΔL*+2kδ(t)}.

According to the embodiment, the output signal from the amplifier 11 is inputted to 1-th, 2-th, ..., L-th lock-in amps 12-1, 12-2, ..., 12-L, reference signals having frequencies Mf of multiples of M {M=2m-1 (m is any of 1, 2, ...): odd number} of the fundamental frequency f of the output signal from the oscillator 10 inputted to PZT5 are formed by frequency multipliers 16-j (j≠1) and inputted to the lock-in amps 12-j (j is any of 1, 2, ..., ), reference signals having frequencies Nf of multiples of N {N=2n (n is any of 1, 2, ..., ): even number} of the fundamental frequency f of the output signal of the oscillator 10 inputted to the PZT5 are formed by the frequency multipliers 16-k and inputted to the lock-in amps 12-k (k≠j, k is any of 1, 2, ..., ), in the first lock-in amp 12-1, the amplitude $V_{2m-1}$ of the signal component having the angular frequency Mω {M=2m-1 (m is any of 1, 2, ... ): odd number}, and the amplitude $V_{2n}$, of the signal component having the angular frequency Nω {N=2n (n is any of 1, 2, ...): even number} is measured and Equation (7) is calculated from Equation (5) and Equation (6).

$$2V^* = \sqrt{\frac{V_{2m-1}^2}{J_{2m-1}^2(2kA)} + \frac{V_{2n}^2}{J_{2n}^2(2kA)}} \quad (7)$$

Or, in Equation (5) and Equation (6), a summation $\Sigma n$ in respect of $n=1, 2, \ldots, n_{max}$ and a summation $\Sigma m$ in respect of $m=1, 2, \ldots, m_{max}$ are carried out to provide Equation (8) and Equation (9) and $V^*$ can be calculated by Equation (10) ($n_{max}$ and $m_{max}$ are predetermined integers). The right hand side of Equation (10) is not dependent on $k\Delta L$ and accordingly, according to Equation (10), $V^*$ can be calculated accurately.

$$\Sigma_n V_n = 2V^* \cos(2k\Delta L) \Sigma_n J_{2n}(2kA) \quad (8)$$

$$\Sigma_m V_{2m-1} = 2V^* \sin(2k\Delta L) \Sigma_m J_{2m-1}(2kA) \quad (9)$$

$$2V^* = \sqrt{\frac{\sum_m V_{2m-1}^2}{\sum_m J_{2m-1}^2(2kA)} + \frac{\sum_n V_{2n}^2}{\sum_n J_{2n}^2(2kA)}} \quad (10)$$

When the amplitude $V_1$ of the signal component having the angular frequency $\omega$ is measured at the first lock-in amp 12-1 and the amplitude $V_2$ of the signal component having the angular frequency $2\omega$ is measured at the second lock-in amp 12-2, Equation (11) is provided by setting $m=n=1$ in Equation 7.

$$2V^* = \sqrt{\frac{V_1^2}{J_1^2(2kA)} + \frac{V_2^2}{J_2^2(2kA)}} \quad (11)$$

The signal processing unit 14 calculates a value of the right hand side of Equation (7) or Equation (10) from measured values $V_{2m-1}$, $V_{2n}$, $J_{2m-1}(2kA)$ and $J_{2n}(2kA)$. As is apparent from Equation (7) or Equation (10), the value of the right hand side of Equation (7) or Equation (10) receives almost no influence of the variation with time of $\Delta L$ and according to the method of the embodiment, the sufficiently stable measurement is carried out without receiving variation with time of $\Delta L$ by thermal expansion or the like. Further, the lock-in amps are used for detecting a signal and accordingly, the signal band width can be made far narrower than that in the case of using only a high-pass filter and high signal-to-noise ratio is provided. For example, in the case of frequency 1 KHz, in lock-in detection with time constant 1 sec, in the lock-in detection, the reception band is equal to or smaller than 1/1000 of that in the case of using only a high-pass filter and the signal-to-noise ratio becomes about 30 times as large as that of the latter case.

Figure 2:
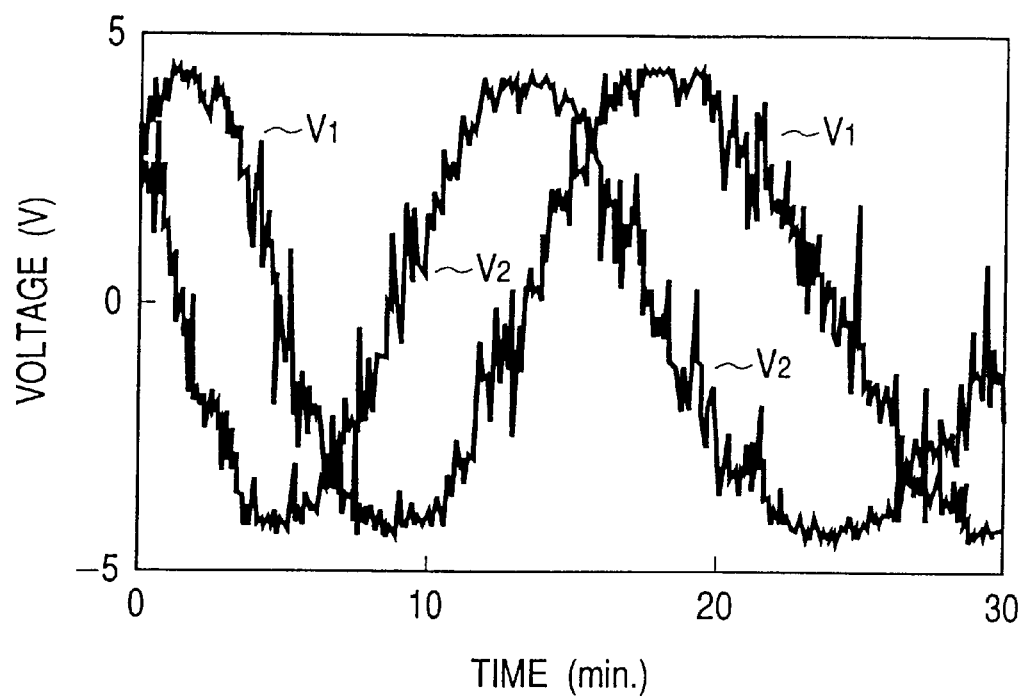
FIG. 2 is a diagram showing an example of time-sequential changes of an amplitude $V_1$ of a signal component having an angular frequency $\omega$ and an amplitude $V_2$ of a signal component having an angular frequency $2\omega$ according to the first embodiment.
Figure 3:
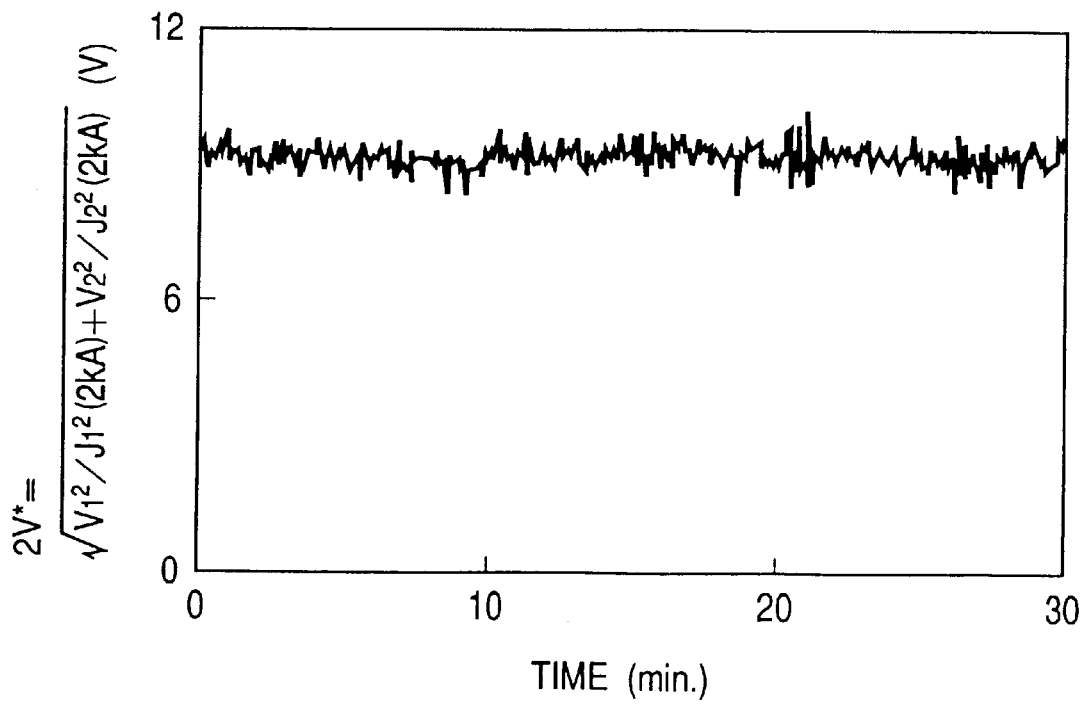
FIG. 3 is a diagram showing a time-sequential change of a result removed of influence of the time-sequential changes of the amplitudes $V_1$ and $V_2$ shown by FIG. 2.

FIG. 2 and FIG. 3 show an example of a result of measurement according to the embodiment. FIG. 2 and FIG. 3 show a result of measuring light reflected from a glass substrate with the glass substrate in air as a sample. FIG. 2 is a diagram showing an example of time-sequential changes of an amplitude $V_1$ of the signal component having an angular frequency $\omega$ and an amplitude $V_2$ of a signal component having an angular frequency of $2\omega$. As is apparent from FIG. 2, $\Delta L$ is varied by one wavelength or more in a time period of 30 minutes and both of the amplitudes $V_1$ and $V_2$ are varied significantly in accordance with the variation. From piezoelectric constant of 0.08 $\mu$m/V of the used PZT5, an amplitude of 2.2 V of an output signal from the oscillator 10 applied to PZT5 and a wavelength of 840 nm of a super luminescent diode (SLD) used as the light source 1, $2kA = 2 \times \{2\pi/(840 \times 10^{-9})\} \times 0.08 \times 10^{-6} \times 2.2 = 2.633$.

FIG. 3 is a diagram showing a time-sequential change of $V^*$ as a result of removing influence of time-sequential changes of amplitudes $V_1$ and $V_2$ shown by FIG. 2 by calculating the right hand side of Equation (11) by the signal processing unit 14 by using the value of 2kA. As is apparent from FIG. 3, there is provided a sufficiently stable value over 30 minutes. That is, an average value of $V^*$ is varied by 1% or smaller in a time period of 30 minutes. Further, noise superposed on the average value of $V^*$ is about 10% at maximum. According to the embodiment, the lock-in amps of unit phase are used, the frequency of the reference signal is set to 1 kHz and the time constant is set to 300 ms, an equivalent noise band width is a very narrow band of 1 Hz or smaller and there is realized a measurement of low noise capable of detecting power of about 1 photon per second. The accuracy of the measurement is 3% rms.

Figure 4:
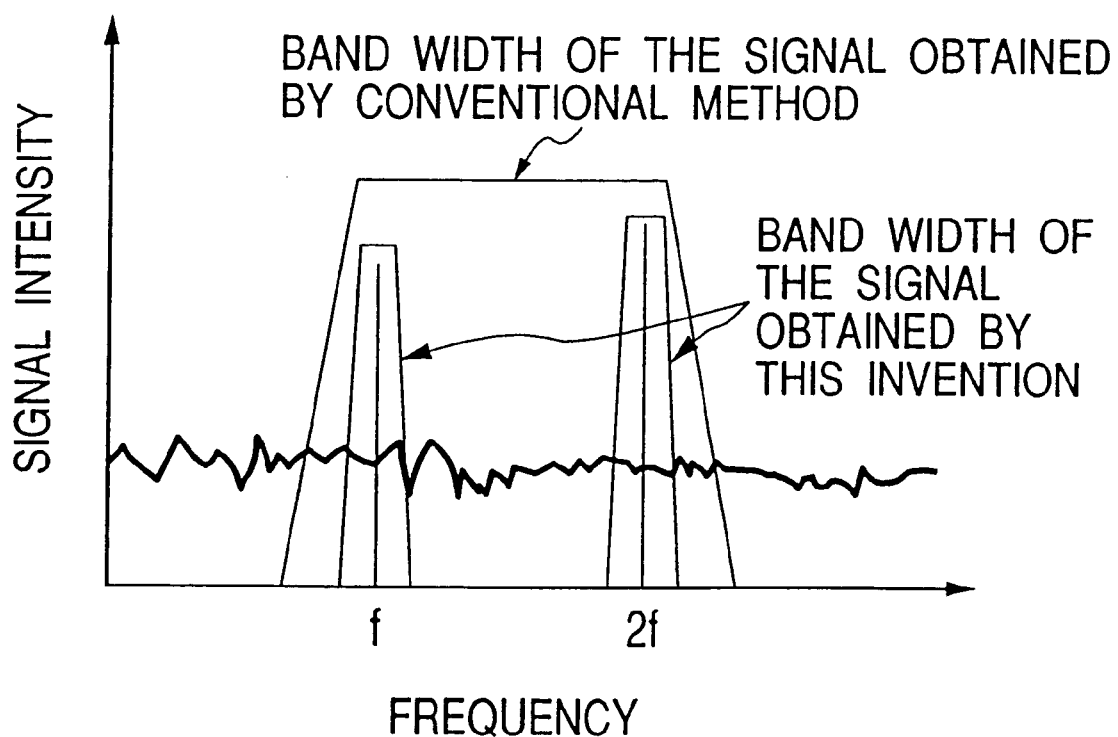
FIG. 4 is a diagram showing a comparison between signal band widths in signal processings of a conventional technology and the first embodiment.

FIG. 4 is a diagram comparing signal band widths in signal processings of a conventional technology and the embodiment. For example, according to the conventional technology with the modulation frequency of 1 kHz, in order to avoid considerable fluctuation of a signal derived from the variation of $\Delta L$, the signal band width of signal processing needs to take about 1 kHz, however, according to the embodiment, the considerable fluctuation of the signal derived from the variation of $\Delta L$ can be avoided, further, the signal band width can be restricted to about 1 Hz and an improvement of S/N by about 30 times can be realized and accordingly, there is provided a result similar to that in the case of using a light source of 30 mW by using a light source of 1 mW. When output of a light source stays the same, in measuring a sample having a considerable scattering or attenuation of light (for example, a sample doped with a colorant, a sample strongly absorbing light as in blood or the like), information of a deeper position (portion) can be provided. That is, when notation $P_{in}$ designates power of incident light (frequency of light is $\nu$), notation $R_b$ designates a reflectivity or a backscattering coefficient of the predetermined point in the sample, an extinction coefficient of light in the sample is designated by notation $\mu$, notation h designates Plank's coefficient and notation B designates band of the detection system, there is provided information at a portion of depth d satisfying $$d < \frac{1}{2\mu} \cdot \log_e\left(p_{in} \cdot \frac{R_b}{h\nu B}\right).$$

Further, even when the lock-in amps are not used in the constitution of FIG. 1, the output signal from the amplifier 11 is inputted to an A-D converter, sampling is carried out at a sampling frequency which is larger than either of $2(2m-1)f$, $4nf$ and the amplitudes $V_{2m-1}$, $V_{2n}$ (for example, $V_1$, $V_2$) of the signal components are calculated by using a Fourier transformer or by Fourier transformation in the signal processing unit 14, $V^*$ is provided from Equation (7) or Equation (10) (for example, Equation (11)). Further, although according to the above-described explanation, the phase of the reference light is modulated by attaching the reference mirror 4 to PZT5, a similar result is naturally provided even when the reference mirror is fixed and not vibrated and the sample is attached to PZT5 and phase of the signal light is modulated.

(Second Embodiment)

Figure 5:
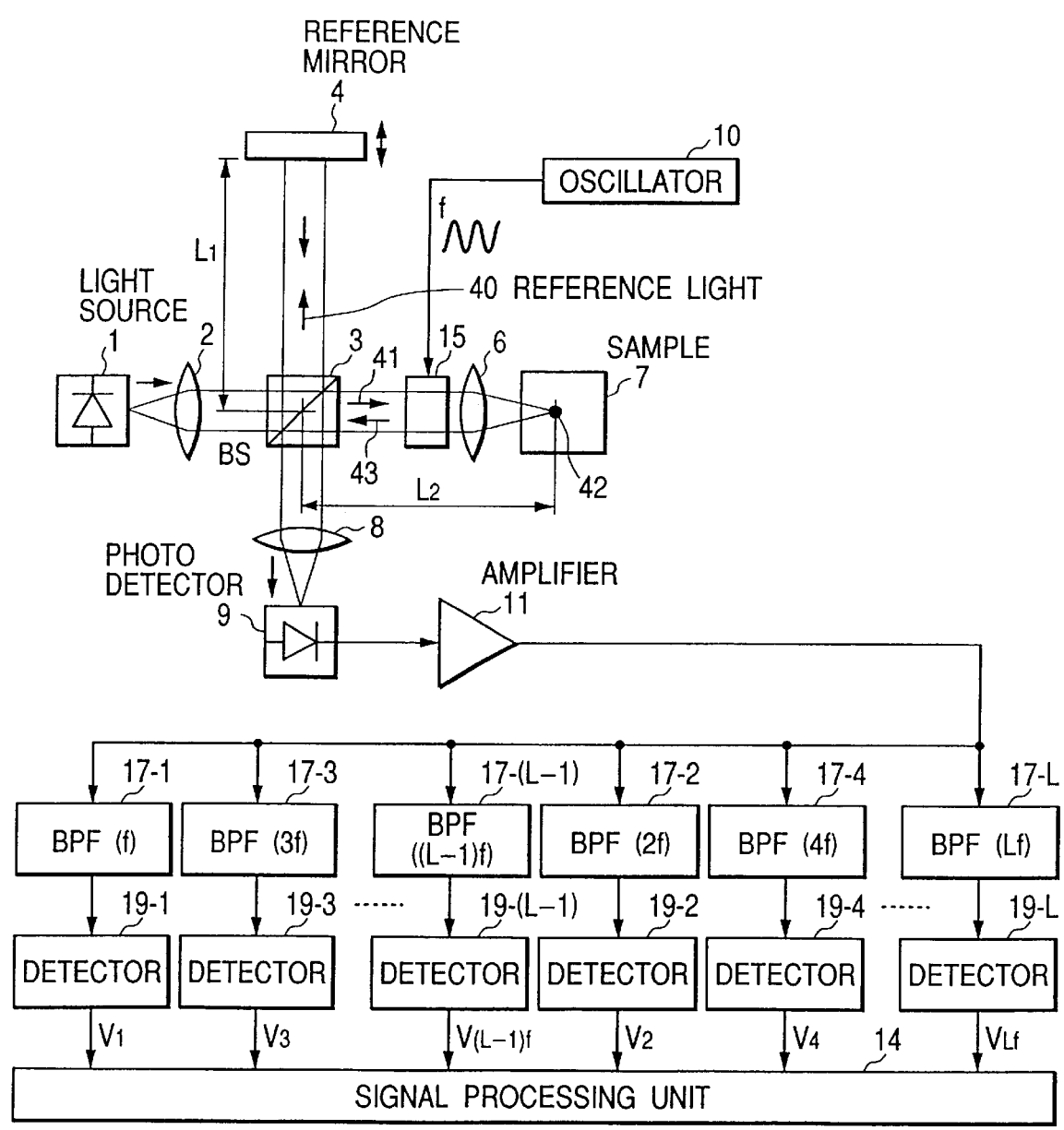
FIG. 5 is a diagram showing a constitution of an inspection apparatus using an optical interferometer according to a second embodiment of the present invention.

FIG. 5 is a diagram showing a constitution of an inspection apparatus using an optical interferometer according to a second embodiment of the present invention. Basically, the constitution of the embodiment is substantially similar to the constitution of the first embodiment. Points which differ from the constitution of the first embodiment resides in that in place of modulating the optical-path length $L_1$, there is used an electro-optic modulator 15 by which the incident light 41 and the signal light 43 are subjected to phase modulation by the fundamental frequency 5 MHz and inputted to band-pass filters 17-1, 17-2, ..., 17-L respectively having central frequencies of 5 MHz, 10 MHz ..., (5×L) MHz which are 1 time, 2 times, ..., L times as large as the modulation fundamental frequency of 5 MHz and having the band width of 100 kHz in place of the plurality of lock-in amps 12-1, 12-2, ..., 12-L and outputs from the band-pass filters 17-1, 17-2, ..., 17-L are respectively inputted to detectors 19-1, 19-2, ..., 19-L to thereby calculate $V_1^2$, $V_2^2$, ..., $V_L^2$ by square-law detection.

Further, according to the constitution of the embodiment in which modulation is carried out by inserting the electro-optic modulator 15 in the optical path of the incident light 41, there is no amplitude modulation of the reference light having large amplitude and measurement having small offset error can be realized. Although according to ideal phase modulation, there is no amplitude modulation, according to real phase modulation, there causes slight amplitude modulation. Generally, the amplitude of the reference light is larger than the amplitude of the signal light and therefore, influence by the amplitude modulation is reduced by the phase modulation of the signal light 43. Further, according to the constitution of the embodiment, there is achieved an effect in which band width of modulation frequency and band width in detecting operation are large, measurement at higher speed can be carried out and the constitution can deal with also a case in which a sample is moved or vibrated in in vivo measurement of biomedical tissue or the like. For example, according to the embodiment, the band-pass filters having the band width of 100 kHz or larger are used, the time constants are set to about 6 μsec or smaller and accordingly, influence of body motion of biomedical tissue is inconsiderable.

Further, according to the constitution of FIG. 5, V* is provided from Equation (7) and Equation (10) (for example, Equation (11)) even when the band-pass filters and the detectors are not used, the output signal from the amplifier 11 is inputted to an A-D converter and sampled at a sampling frequency satisfying the sampling theorem and amplitudes of signal components $V_{2m-1}$ and $V_{2n}$ (for example, $V_1$, $V_2$) are calculated by using Fourier transformer or by Fourier transformation in the signal processing unit 14.

(Third Embodiment)

Figure 6:
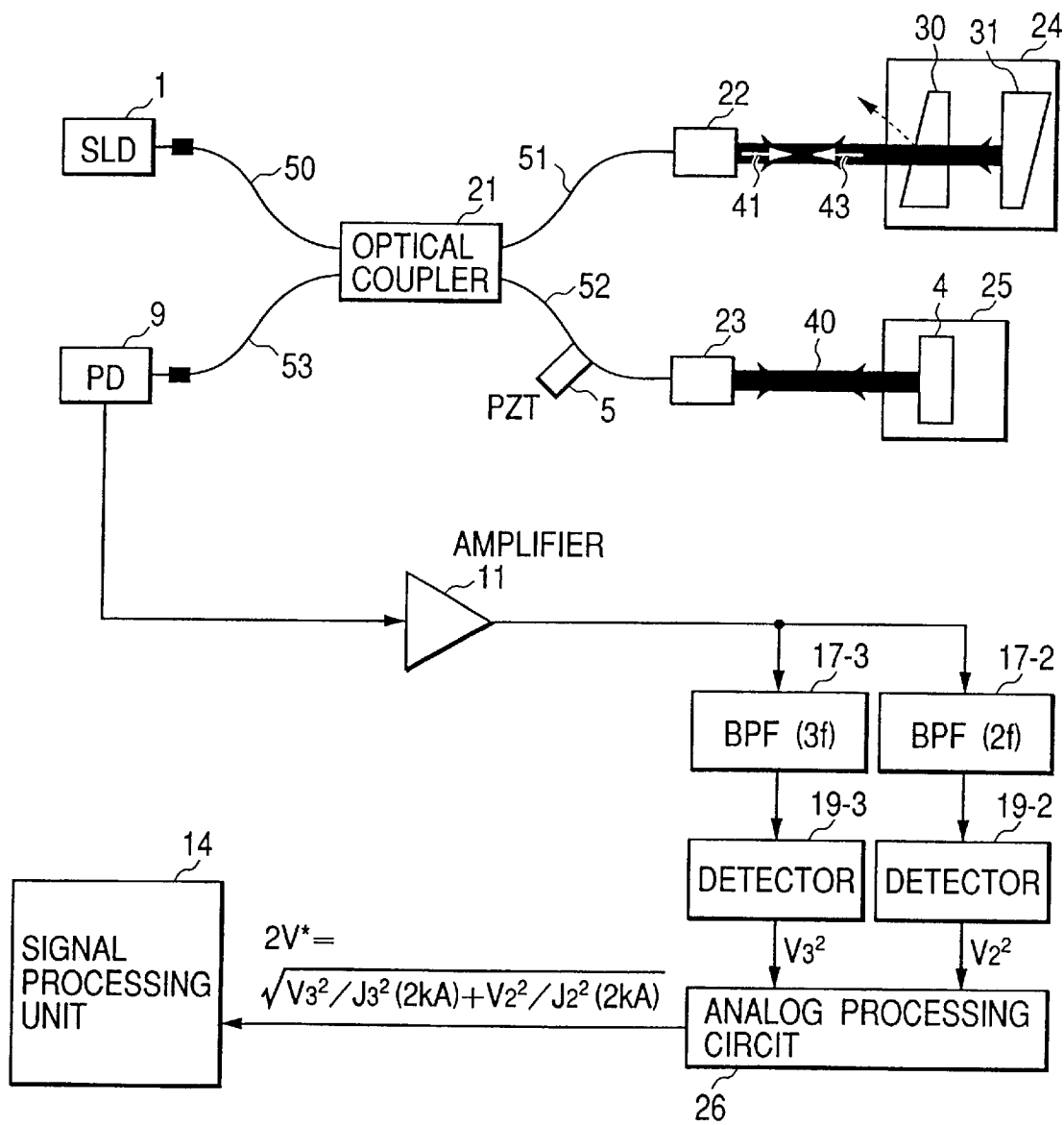
FIG. 6 is a diagram showing a constitution of an inspection apparatus using an optical interferometer according to a third embodiment of the present invention.

FIG. 6 is a diagram showing a constitution of an inspection apparatus using an optical interferometer according to a third embodiment of the present invention. According to the embodiment, a low coherent optical interferometer similar to those in the first and the second embodiments is constituted by using an optical coupler 21. The light source 1 and the photo detector 9 are the same as the light source and the photo detector used in the first and the second embodiments. However, the output from the super luminescent diode (SLD) used as the light source is not collimated by a lens, the output from the SLD chip is directly coupled to an optical fiber 50 to thereby constitute fiber pigtail and to thereby eliminate loss by an optical system of lens for collimation or the like and the light from the super luminescent diode 1 is introduced efficiently to the optical fiber 50 connected to the optical coupler 21. Light introduced into the optical coupler 21 by the optical fiber 50 is branched in two by the optical coupler 21 of 2×2 (inlet port number; 2, outlet port number; 2) and formed into parallel light fluxes respectively by collimate lenses 22 and 23. The parallel light flux produced by the collimate lens 22 is irradiated on the sample 7 comprising wedge plates 30 and 31 placed on a stage 24 and the parallel light flux produced by the collimate lens 23 is irradiated orthogonally on the reference mirror 4.

Faces of the two wedge plates 30 and 31 opposed to each other are installed in parallel and the parallel light flux produced by the collimate lens 22 is incident orthogonally on the opposed faces. Light reflected by the wedge plates 30 and 31 as signal light and light reflected by the reference mirror 4 as reference light are respectively introduced into optical fibers 51 and 52 by the lens 22 and the lens 23 again in the reverse direction. The reference light and the signal light are combined by the optical coupler 21 and are detected by the photo detector 9 optically connected to the optical fiber 53 connected to the optical coupler 21.

According to the embodiment, the difference between optical-paths of the signal light and the reflected light is changed by moving the reference mirror 4 and a very small distance between the wedge plates 30 and 31 opposed to each other in parallel can be measured. The reference mirror 4 attached to a linear motion stage 25 is moved in a progressing direction of the reference light. Only when an optical-path of either of the reflected light from the wedge plate 30 or the reflected light from the wedge plate 31 and an optical-path length of the reference light coincides with each other within the coherence length of the light source, the signal light is detected by the photo detector 9. The wedge plates 30 and 31 are constituted by glass.

According to the embodiment, phase modulation of the reference light is carried out by using PZT5 and vibration is provided to the optical fiber by PZT5 and large phase modulation is provided by an amplitude far smaller than an amplitude of vibration when the phase modulation is carried out by directly vibrating the mirror (since refractive index of fiber is changed sensitively by vibration). When phase modulation is carried out by vibrating the mirror directly by PZT5 to a degree of wavelength-of light, a stacking piezoelectric vibrator is needed to use as PZT5. In the case of a single layer of a piezoelectric vibrator, a displacement amplitude per driving voltage 1 V falls in a range of several nm through 10 nm, and when vibration having a such degree of displacement amplitude is provided to an optical fiber, it seems that phase modulation to the degree of wavelength of light can be provided to output light from the optical fiber. Further, by constituting an optical-path by an optical fiber, the optical fiber operates as a spatial filter (light having different direction is not irradiated on the detector), the efficiency of interference is promoted and stability of the detected signal is increased.

According to the embodiment, the constitution of carrying out signal processing after detecting light by the photo detector 9 is the same as the constitution of the second embodiment. According to the embodiment, different from the second embodiment, it is not the fundamental frequency component $V_1$ of the modulation frequency but third order harmonics component $V_3$ of the fundamental frequency of the modulation frequency is measured and accordingly, influence of electric leakage of the modulation signal is not received (since a signal having a frequency different from the frequency of the modulation signal is detected) and low offset measurement is realized. Outputs of the square detectors 19-1, 19-2 are outputted to an analog processing circuit 26 and the right hand side of Equation (12) is calculated by analog calculation to thereby accelerate speed of signal processing.

$$2V^* = \sqrt{\frac{V_2^2}{J_2^2(2kA)} + \frac{V_3^2}{J_3^2(2kA)}} \quad (12)$$

Figure 7:
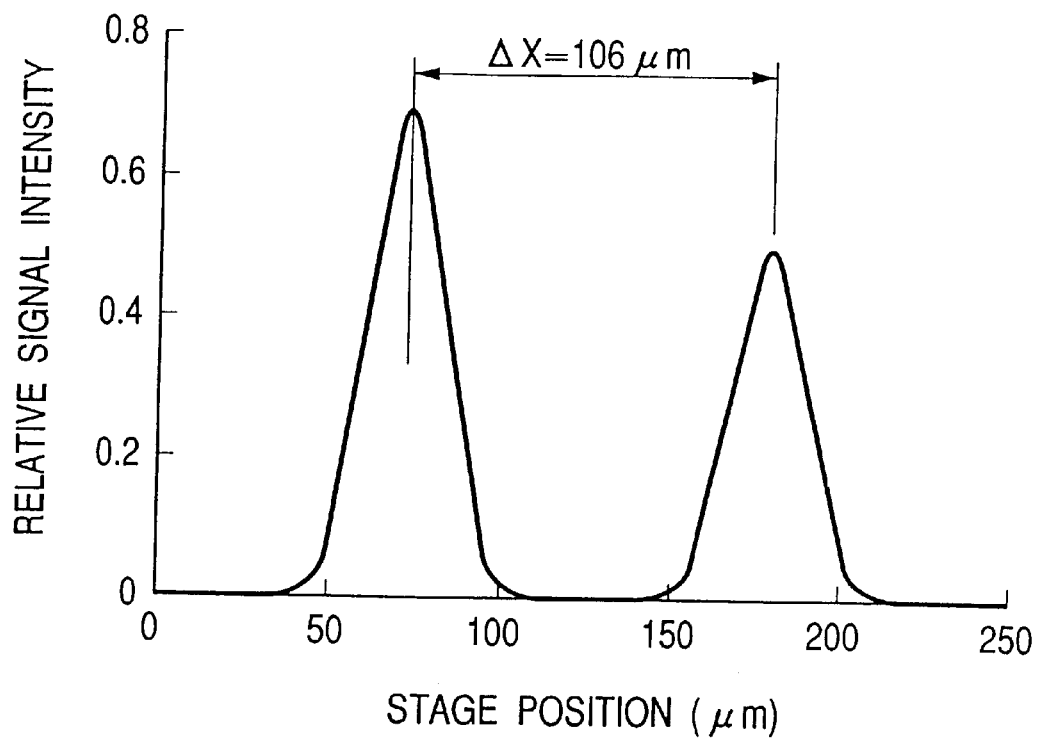
FIG. 7 is a diagram schematically showing position X of a stage and a change of an intensity of a detected signal.

FIG. 7 schematically shows a position X of the stage 25 and a change in the detected signal intensity according to the embodiment. There are two peaks in correspondence with the reflected light from the wedge plate 30 and the reflected light from the wedge plate 31. A distance of 106 μm between the two peaks corresponds to a value of ½ of a distance between the parallel faces of the wedge plates (212 μm). A position of a center of the peak which is actually detected is determined by an accuracy of 1 μm by applying Gaussian function. According to the embodiment, a small clearance which is difficult to measure by a micrometer or the like can be measured by an accuracy of micron meter order.

Further, according to the constitution of FIG. 6, V* is provided by Equation (7) or Equation (10) (for example, or Equation (12)) even when the band-pass filters, the detectors and the analog processing circuit are not used and the output signal from the amplifier 11 is inputted to an A-D converter and sampled by a sampling frequency satisfying the sampling theorem (a frequency two times or more as large as through frequencies of the band-pass filters) and the amplitudes $V_{2m-1}$ and $V_{2n}$ (for example, $V_2$ and $V_3$) of the signal components are calculated by using a Fourier transformer or by Fourier transformation in the signal processing unit 14.

According to the invention, stable signal detection having no drift of signal caused by thermal expansion or mechanical backlash and narrow band reception for achieving high-sensitivity characteristic near to quantum noise limit particular to signal detection by an optical interferometer, are simultaneously carried out, a signal having high stability where fluctuation of the signal is within several % over one hour, can be provided with high signal-to-noise ratio and in measurement of a sample of biomedical tissue or the like having large scattering or attenuation of light (for example, dye-suspended sample, blood or the like), distribution of refractive index or extinction coefficient can be measured accurately up to a portion having a large depth of 1 mm or more (with error of 0.1% in a sample having a thickness of 0.1 mm).

Further, although Equation (4), Equation (6) and Equation (7) are equations when the reference light is subjected to phase modulation by vibrating the mirror for reflecting the reference light with the amplitude of A such that the average difference between the optical-paths of the reference light and the signal light becomes ΔL, Equation (4), Equation (6) and Equation (7) can further be generalized. Equation (3) can be generalized to Equation (3') by designating the average optical path difference of the reference light and the signal light by notation D, designating the amplitude in the phase modulation of the reference light by θ=2kA and designating notation φ as an arbitrary constant and at this occasion, the phase difference between the reference light and the signal light becomes Equation (13).

$$L_1(t) = L_2 + \frac{D}{2} + \frac{\theta}{2k}\sin(\omega t + \phi) \quad (3')$$

$$2k\{L_1(t) - L_2\} = kD + \theta\sin(\omega t + \phi) \quad (13)$$

By substituting Equation (13) and Equation (2), Equation (4'), Equation (5') and Equation (6') respectively in correspondence with Equation (4), Equation (5) and Equation (6) are provided.

$$V(t) = V_{DC} + V^*\cos\{kD + \theta\sin(\omega t + \phi)\} \quad (4')$$
$$= V_{DC} + V^*\cos(kD)J_0(\theta) +$$
$$2V^*\cos(kD)\sum J_{2n}(\theta) \times \cos\{2n(\omega t + \phi)\} -$$
$$2V^*\sin(kD)\sum J_{2n-1}(\theta) \times \sin\{(2n - 1)(\omega t + \phi)\}$$

$$V_{2n} = 2V^*J_{2n}(\theta)\cos(kD) \quad (5')$$

$$V_{2m-1} = 2V^*J_{2m-1}(\theta)\sin(kD) \quad (6')$$

Similarly, in Equation (7) through Equation (12), corresponding equations where θ is replaced by 2kA and D is replaced by 2ΔL are respectively established.

(Fourth Embodiment)

Figure 8:
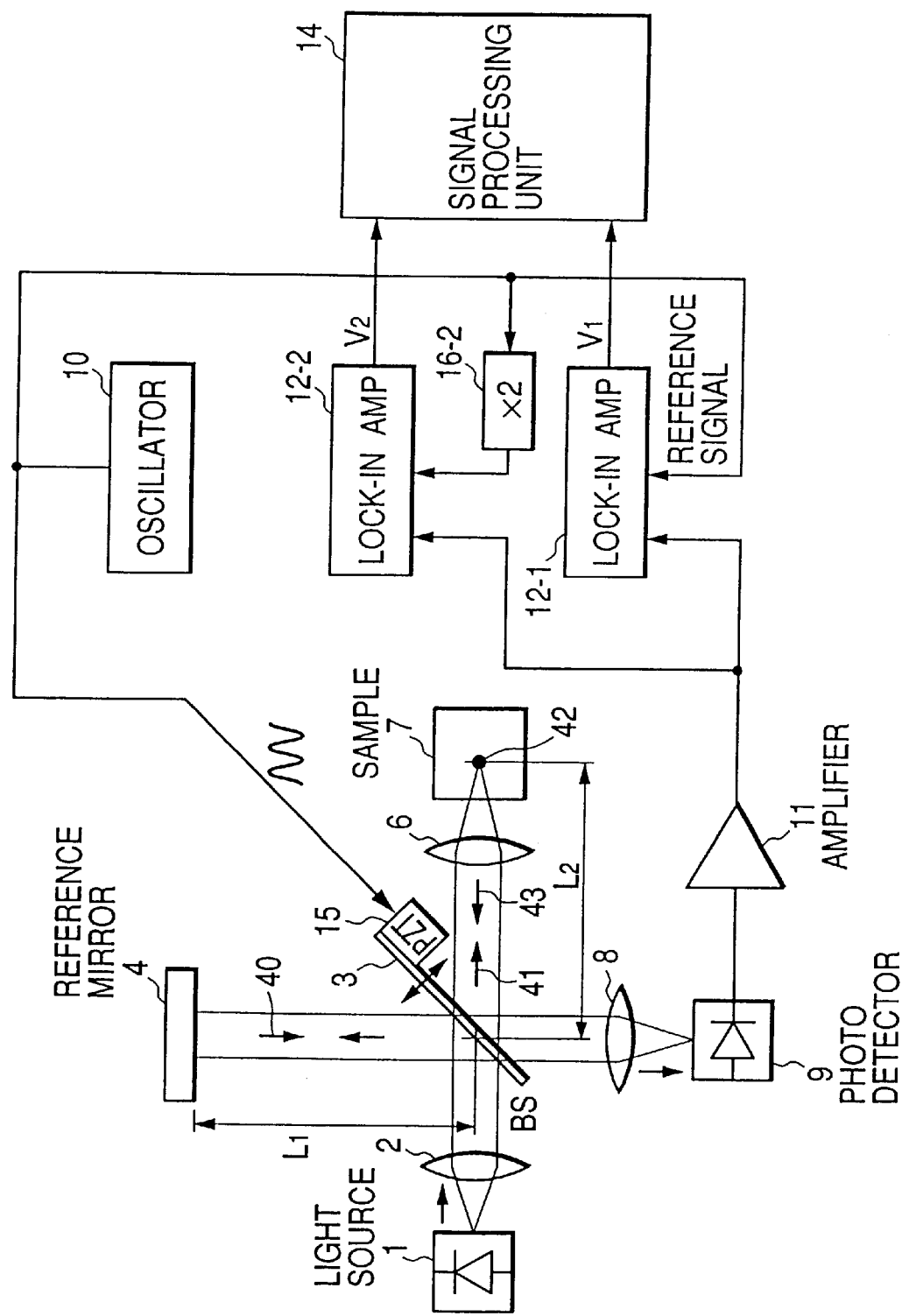
FIG. 8 is a diagram showing a constitution of an inspection apparatus using an optical interferometer according to a fourth embodiment of the present invention.

FIG. 8 is a diagram showing a constitution of an inspection apparatus using an optical interferometer according to a fourth embodiment of the present invention. The fourth embodiment is provided with a constitution basically common to the constitution of the first embodiment and is different from the first embodiment in that the reference mirror 4 is not vibrated and the beam splitter 3 is vibrated by PZT5 in a direction of 45 degree relative to the reference light 40 and the incident light 41. According to the constitution of FIG. 8, the reference light 40 and the signal light 43 are subjected to phase modulation and when the displacement of PZT5 in the vibrating direction is expressed as A sin(ωt) similar to the first embodiment, Equation (4"), Equation (5") and Equation (6") in correspondence with Equations where D is replaced by 2ΔL and θ is replaced by $2\sqrt{2}kA$ in Equation (4'), Equation (5') and Equation (6') are respectively established.

$$V(t) = V_{DC} + V^*\cos\{2k\Delta L + 2\sqrt{2}kA\sin(\omega t + \phi)\} \quad (4'')$$
$$= V_{DC} + V^*\cos(2k\Delta L)J_0\{2\sqrt{2}kA\} +$$
$$2V^*\cos(2k\Delta L)\sum J_{2n}\{2\sqrt{2}kA\} \times \cos\{2n(\omega t + \phi)\} -$$
$$2V^*\sin(2k\Delta L)\sum J_{2n-1}\{2\sqrt{2}kA\} \times \sin\{(2n - 1)(\omega t + \phi)\}$$

$$V_{2n} = 2V^*J_{2n}\{2\sqrt{2}kA\}\cos(2k\Delta L) \quad (5'')$$

$$V_{2m-1} = 2V^*J_{2m-1}\{2\sqrt{2}kA\}\sin(2k\Delta L) \quad (6'')$$

In the following, by using Equation (5") and Equation (6"), Equation (7) through Equation (12) are calculated.

According to the embodiment, to provide phase modulation having the same magnitude, in comparison with the first embodiment, there is achieved an effect in which the amplitude of vibration of PZT5 is reduced by $1/\sqrt{2}$. Further, although according to the embodiment, as the phase modulator for modulating the reference light 40 and signal light 43, the beam splitter 3 vibrated by PZT5 is aligned, substantially the same effect is achieved by a constitution in which the beam splitter 3 is vibrated similar to the embodiment by switching only positions of the sample 7 and the reference mirror 4 to thereby modulate phases of the incident light 41 and the reference light 40.

(Fifth Embodiment)

Figure 9:
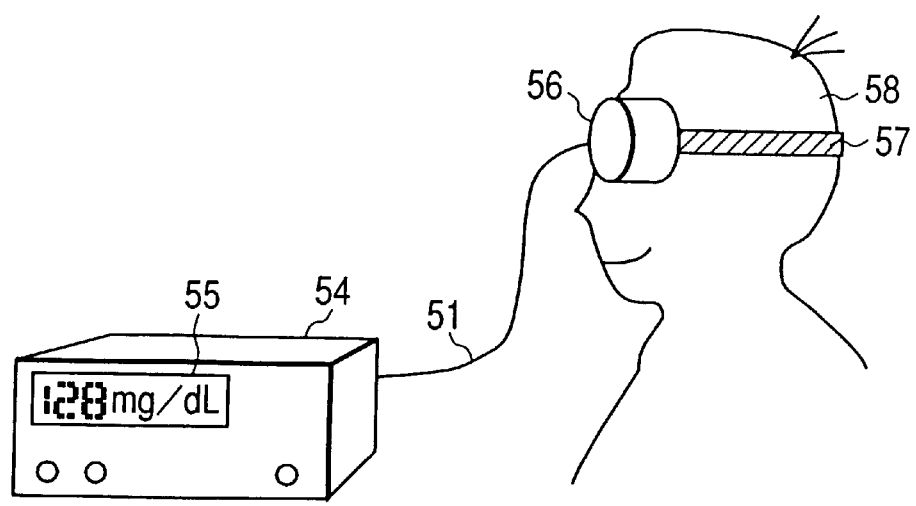
FIG. 9 is a view showing a constitution of a noninvasive blood glucose level monitoring apparatus using an optical interferometer according to a fifth embodiment of the present invention.
Figure 10:
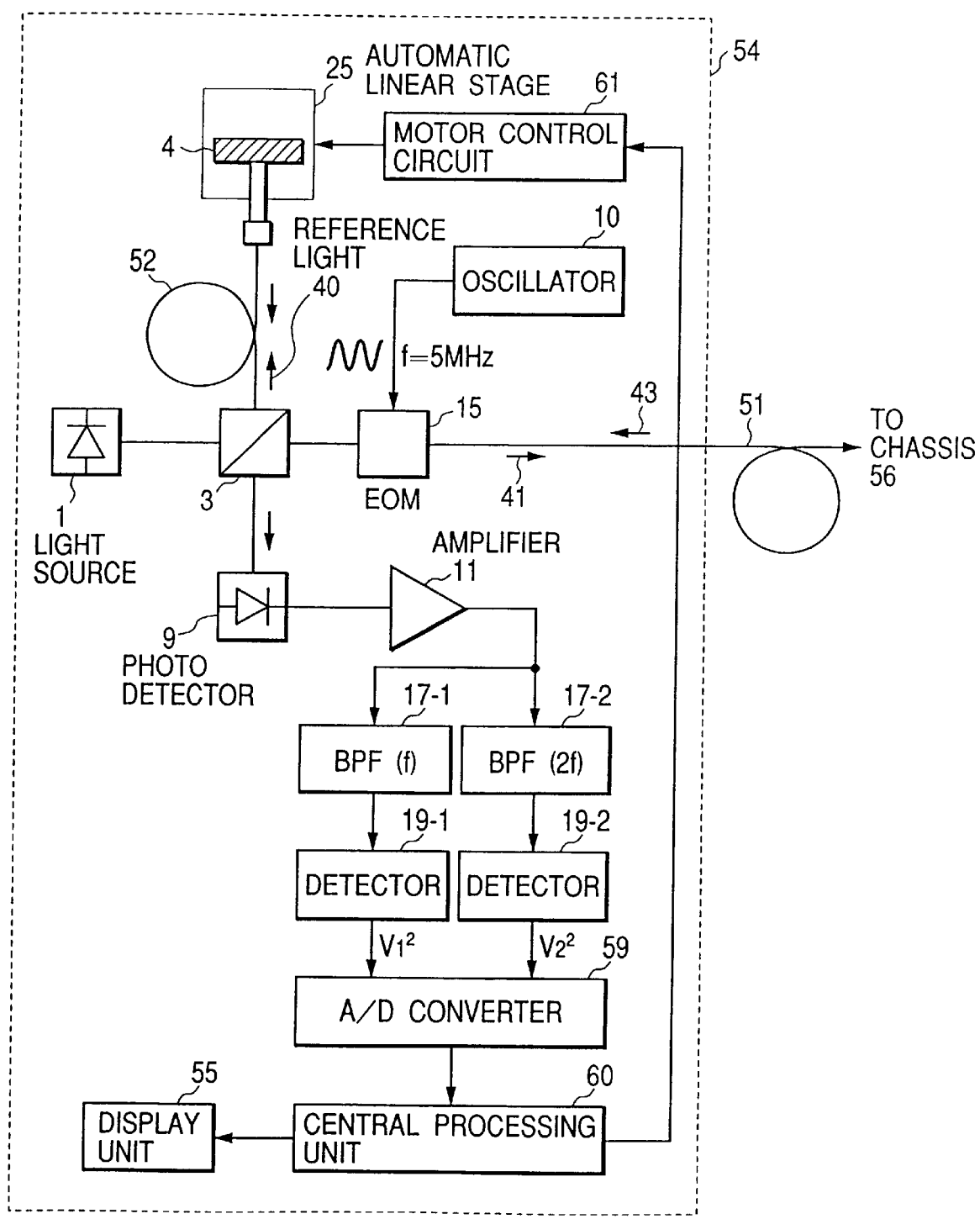
FIG. 10 is a diagram showing a detailed constitution of a first chassis constituting the noninvasive blood glucose level monitoring apparatus according to the fifth embodiment.
Figure 11:
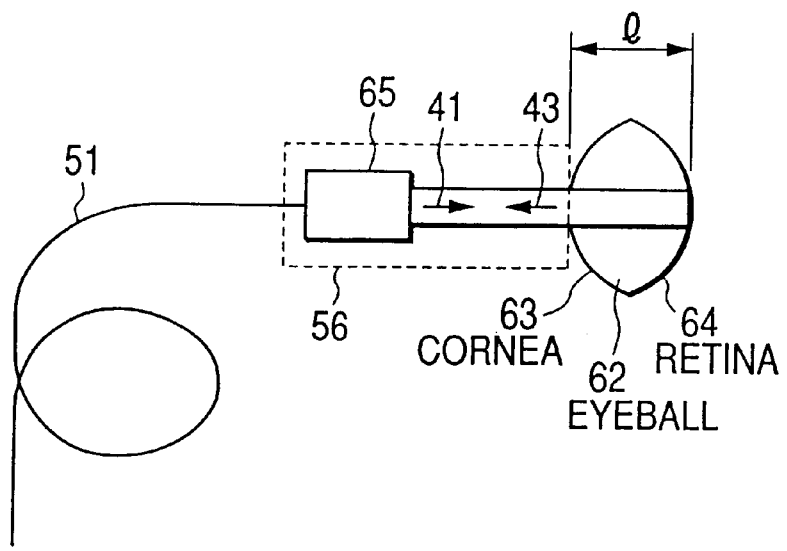
FIG. 11 is a view showing a detailed constitution of a second chassis constituting the noninvasive blood glucose level monitoring apparatus according to the fifth embodiment.
Figure 12:
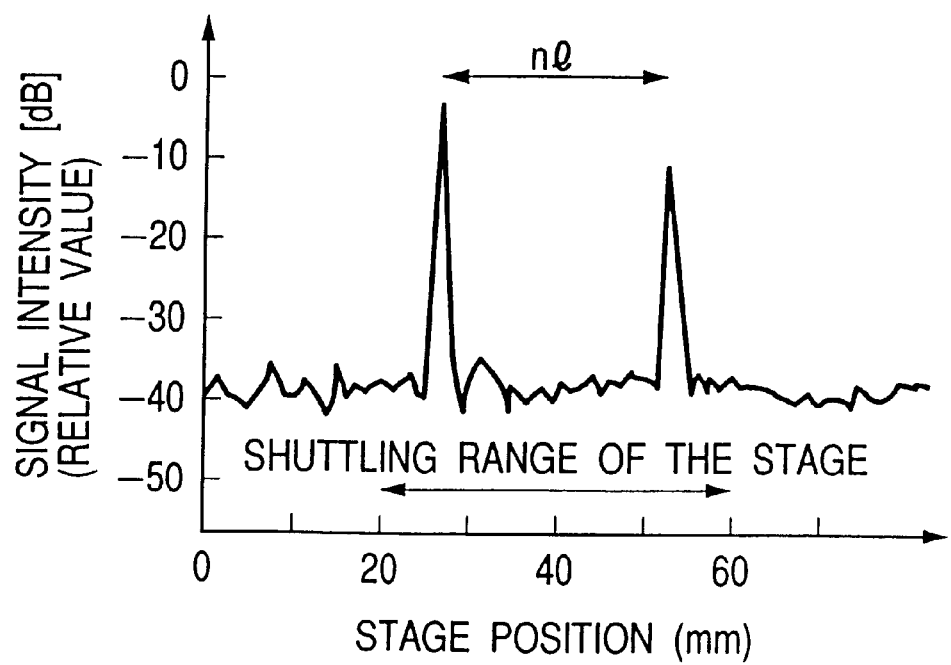
FIG. 12 is a diagram schematically showing a measured value provided by the noninvasive blood glucose level monitoring apparatus according to the fifth embodiment.

FIG. 9 is a diagram showing a constitution of a noninvasive blood glucose monitoring level using an optical interferometer according to a fifth embodiment of the present invention. FIG. 10, FIG. 11 and FIG. 12 are respectively diagrams showing detailed constitutions of first and the second chassis constituting the noninvasive blood glucose level monitoring apparatus according to the embodiment and a diagram schematically showing a measured value provided by the noninvasive blood glucose level monitoring apparatus according to the embodiment. According to the embodiment, there is used a principle in which a concentration of glucose of aqueous humor of the eye (body liquid in the eyeball) which is known to change excellently in accordance with a change in the blood glucose level, is calculated by a change in the extinction coefficient at the inner portion of the eyeball. The noninvasive blood glucose level monitoring apparatus shown by FIG. 9 is constituted by a second chassis 56 fixed to the head portion of a test subject 58 by an expandable band 57, the optical system for exposing a sample (eyeball of the test subject 58) under light, a first chassis 54 containing the detecting system of signal light and a signal processing system and including a display unit 55 for displaying a result of the provided blood glucose level and an optical fiber 51 for connecting the first chassis 54 and the second chassis 56. There is constructed a constitution in which the second chassis 56 is attached with the expandable band 57 and is fixed to the head portion of the test subject 58 by the band 57 and the second chassis 56 is fixed to the position of the eyeball of the test subject 58 to thereby expose the eye under light.

FIG. 10 shows a detailed constitution of the first chassis 54. Near infrared light having a wavelength of 700 nm through 2500 nm is provided with a constitution in which permeability into a biomedical tissue is comparatively excellent in electromagnetic wave of a region from infrared ray to vacuum ultra violet, that is, in electromagnetic wave having a wavelength of 200 nm through 20000 nm, permeates a biomedical sample having a thickness to a degree of several mm and can be used in optical measurement of biomedical tissue. In measuring the blood glucose level, that is, the glucose concentration in blood, absorption wavelength of glucose in the near infrared region may be used. As absorption wavelengths of glucose in the near infrared region, there are known 1030 nm, 1200 nm, 1580 nm, 2280 nm and so on. However, in the near infrared region having a wavelength of 700 nm through 2500 nm, in a region having the wavelength of 1400 nm or more, absorption of water is intensified and accordingly, measurement of the glucose concentration at a portion having a thickness of 1 cm or more becomes disadvantageous. According to the embodiment, the eyeball is regarded as a cell for absorption measurement having an optical-path length between the cornea and the retina. The optical-path length of the cell is 1 cm or more and accordingly, it is advantageous to use the wavelength of 1400 nm or less. Absorption of glucose relative to absorption of water for producing the best contrast of absorption in the region is absorption in the band of 1030 nm.

Figure 13:
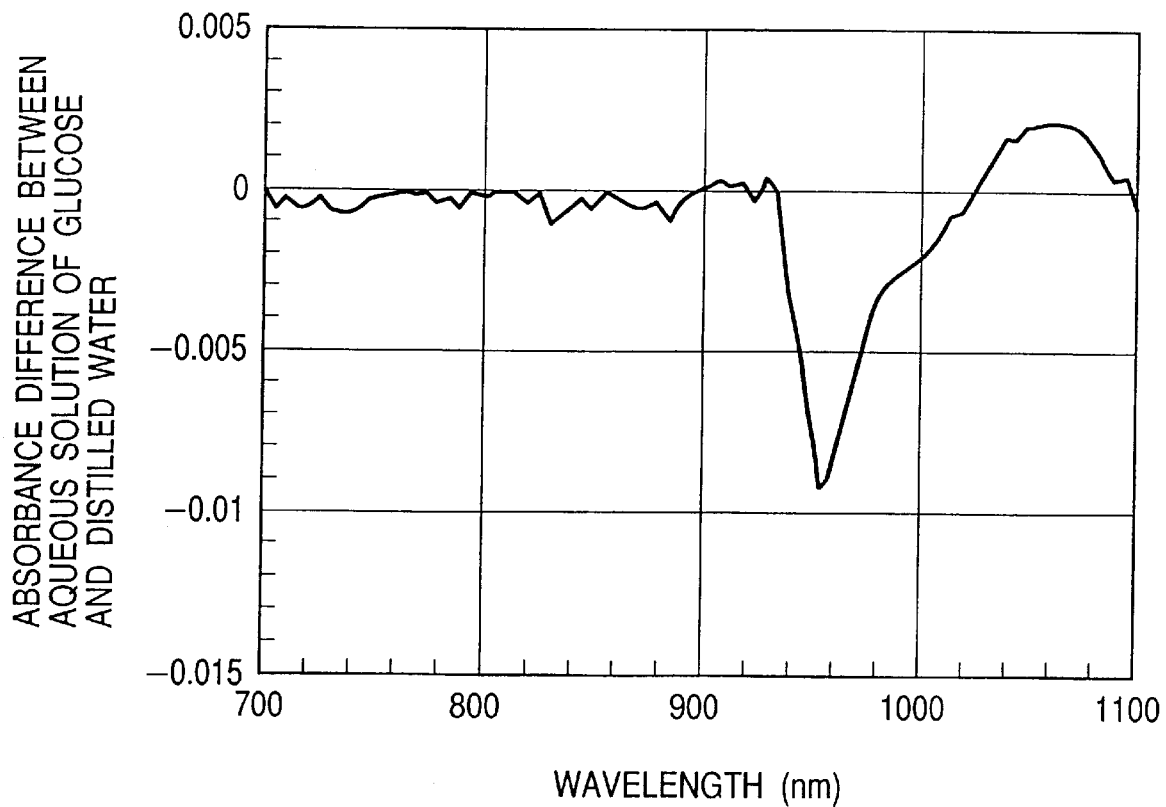
FIG. 13 is a diagram showing spectra of absorbance difference between an aqueous solution of glucose and distilled water.

FIG. 13 shows spectra of absorbance difference of an aqueous solution of glucose and distilled water. A negative peak at 960 nm shows that there is an absorption peak of water at 960 nm and glucose is dissolved and water molecules are reduced and absorption of water molecules at the band of 960 nm is reduced. The negative peak is caused by solvency of an arbitrary substance other than glucose and there is no selectivity with regard to glucose. A peak at 1050 nm is a peak derived from absorption of glucose per se and it seems that the peak of absorption of glucose at 1030 nm is slightly shifted to the long wavelength side by widening the absorption peak of water at 960 nm. According to the embodiment, there is used a tungsten halogen lamp having a flat emission spectrum characteristic over wavelengths of from 400 nm to 2000 nm as the light source 1, a monochromater constituted by a diffraction grating and a slit having a predetermined width are attached to the tungsten halogen lamp and light having a central wavelength of 1050 nm and having spectrum full width at half maximum of 20 nm is emitted from the light source 1. The spectrum width (20 nm) of the light from the light source 1 is smaller than a width of the peak at a vicinity of 1050 nm of FIG. 13 (about 50 nm). The coherence length calculated from the wavelength and the spectrum width of the light from the light source becomes about 24 $\mu$m.

Similar to the first, the second and the fourth embodiment, the light from the light source 1 is split by the beam splitter 3 and one split portion of the light constitutes the reference light 40 by being reflected by the mirror 4 fixed on the automatic linear motion stage 25 having a moving distance of 10 mm and other split portion of the light constitutes the incident light 41 irradiated on the test subject 58. The frequency f of the phase modulation by the electro-optic modulator 15 is 5 MHz and the signal light 43 reflected from the eyeball is subjected to the electro-optic modulator 15 and is combined again with the reference light 40 at the beam splitter 3. Also the reference light 40 is inputted to the optical fiber 52 to thereby gain the optical-path length and optical-path lengths of the signal light 43 and the reference light 40 are made to coincide with each other within the moving distance of the stage 25. The output from the photo detector 9 is respectively inputted to the band-pass filter 17-1 having the central frequency of f=5 MHz and the band-pass filter 17-2 having the central frequency of 2f=10 MHz, the output from the band-pass filter 17-1 is inputted to the detector 19-1 and the output from the band-pass filter 17-2 is inputted to the detector 19-2, respectively and the detectors 19-1 and 19-2 respectively output voltages in proportion to $V_1$ and $V_2^2$.

Further, the band width B of the band-pass filters 17-1, 17-2 is about 100 kHz and the response time of the circuit system (~2/(3.5 B)) is made as fast as about 6 $\mu$s. Output voltages from the detectors 19-1 and 19-2 are digitized by an A-D converter 59 and V* is calculated based on Equation 7 (or Equation 11) at a central processing unit 60. The central processing unit 60 simultaneously controls operation of a motor control circuit 61, shuttles the mirror 4 on the stage 25 once per second, scans the optical-path length of the reference light 40 in a range of 40 mm and scans a location of causing the detected signal light 43.

FIG. 11 is a view showing a detailed constitution of the second chassis 56 and an enlarged constitution of a vicinity of the eyeball (sample) of the test subject on which light is incident. A distal end of the optical fiber 51 for exposing the sample under light is connected to the chassis 56 containing a collimate lens 65. Light emitted from the optical fiber 51 is made into parallel light flux by the collimate lens 65 and is irradiated on the eyeball 62. The inside of the eyeball is comparatively transparent and light scattering is not caused and accordingly, the principal signal light produced in the eyeball is the reflected light from the cornea 63 and the reflected light from the retina 64. The optical-path length between the retina 64 and the cornea 63 is about 30 mm in the case of a grown-up person (30.7 mm when the distance between the retina 64 and the cornea 63 is set to 23 mm and the refractive index of water is set to 1.333). Accordingly, when the mirror 4 is shuttled and the optical-path length of the reference light 40 is varied and the scanning operation is carried out, in the first optical-path length of the reference light 40, a signal based on the reflected light from the cornea is provided and in the second optical-path length which is slightly shifted from the first optical-path length of the reference light 40, a signal based on the reflected light from the retina is provided. That is, when the signal intensity of the signal light detected relative to the position of the stage 25 is plotted, as schematically shown by FIG. 12, there is constituted a curve having two peaks separated from each other by the optical-path length ln between the cornea 63 and the retina 64 (n: refractive index of the eyeball, l; geometrical thickness of the eyeball). The optical-path length nl is calculated from the distance between the two peaks and intensities of the respective signal lights are calculated by values integrating areas of the respective peaks. By light absorption in the eyeball, light transmitting through the eyeball is attenuated and therefore, the intensity of light irradiated on the cornea 63 and the intensity of light irradiated on the retina 64 differs from each other by an amount of the attenuation. By assuming that the reflectivities of the cornea 63 and the retina 64 are constant and setting the extinction coefficient of the inner portion of the eyeball as notation α and setting the area intensities of the two peaks as $S_1$ and $S_2$, by law of Lambert, Equation (14) is established (K is a known constant determined by the reflectivities of the cornea and the retina).

$$\log_{10}\left(\frac{S_1}{S_2}\right) = \frac{2\alpha l}{\log_e 10} + K \quad (14)$$

The extinction coefficient α is provided with a dependency on the glucose concentration C in the aqueous humor of the eye as shown by Equation (15).

$$\alpha = \epsilon C \times \log_e 10 + \alpha_0 \quad (15)$$

where notation ε designates a molar extinction coefficient of glucose and notation $\alpha_0$ designates the extinction coefficient (known) of water per se which is the background. The refractive index n of the eyeball is varied by the glucose concentration. However, a variation of the reflective index n of the eyeball by the glucose concentration is smaller than a change in the extinction coefficient α and accordingly, when the variation is disregarded and the refractive index n of the eyeball is set to a constant value of 1.3, l (geometrical thickness of the eyeball) is calculated from the distance between the peak positions of the measured signal. Further, the extinction coefficient ε of glucose at the absorption wavelength of 1050 nm is known to be $\epsilon = 3.7 \times 10^{-6}$ {(mmol/L)$^{-1}$(cm)$^{-1}$}. By assuming that respective amounts of $\beta_1$ (=2ε), $$\beta_2 = \frac{2\alpha_0}{\log_e 10}$$

are known, Equation (16) is provided from Equation (14) and Equation (15) and the glucose concentration C is calculated from the measured value l by Equation (17).

$$\log_{10}\left(\frac{S_1}{S_2}\right) = \beta_1 C l + \beta_2 l + K \quad (16)$$

$$C = \frac{\log_{10}\left(\frac{S_1}{S_2}\right) - \beta_2 l - K}{\beta_1 l} \quad (17)$$

By carrying out oral glucose tolerance test by oral administration of glucose to the test subject and using Equation (17), a relative change amount of the glucose concentrations C(C(t1), C(t2)) from measured values l (l($t_1$), l($t_2$)) in respect of the same test subject at the different time points $t_1$ and $t_2$ can be calculated from Equation (18) and a change in the glucose concentration on the eyeball of the test subject can easily be known.

$$\Delta C = C(t_2) - C(t_1) \quad (18)$$

According to the embodiment, the band-pass filters having the band width of 100 kHz or more are used, the time constant is set to about 6 μsec and accordingly, the reflected signal from the eyeball can be provided without receiving influence of movement of the eyeball, the relative change of the glucose concentration in the aqueous humor of the eye can be calculated and blood glucose level monitoring can be carried out without drawing blood. Further, V* is provided from Equation (7) or Equation (10), for example, Equation (11) when the band-pass filters and the detectors are not used in the constitution of FIG. 10, the output signal from the amplifier 11 is inputted to the A-D converter 59 and the amplitudes $V_1$ and $V_2$ of the signal component are calculated by sampling the signal at a sampling frequency satisfying the sampling theorem and using Fourier transformer or by Fourier transformation at the signal processing unit 14. Further, the amplitudes $V_{2n}$ and $V_{2m-1}$ of the signal component (Equation (5), Equation (6)) may be calculated by Fourier transformation and Equation (7) through Equation (12) may be calculated.

Although according to the embodiment; reflection at interfaces of the eyeball is utilized, even at a portion of a biomedical tissue having a plurality (at least 2) of interfaces in other arbitrary biomedical tissue where a wall face of a blood vessel, a surface of a blood cell and refractive index are discontinuously changed, by calculating an optical-path length between the plurality of interfaces and attenuation of light between the plurality of interfaces, a method similar to the method in the embodiment is naturally applicable. That is, there can be realized an apparatus of monitoring a blood glucose level by detecting a glucose concentration by calculating an optical-path length between a plurality of interfaces of a tissue in a biomedical tissue and attenuation of light between the plurality of interfaces.

Although according to the embodiment, the eyeball having the optical-path length of 1 cm or more is selected as the measured portion and therefore, the glucose absorption band of the band of 1030 nm is utilized and monochromatic light dispersed from white light source of a halogen lamp is used, by regarding a measured portion having a shorter optical-path length, for example, a capillary or a blood cell per se is regarded as a cell, the glucose absorption band at a vicinity of 1580 nm or 2280 nm having stronger absorption can naturally be utilized. Further, when the glucose absorption band at a vicinity of 1580 nm is utilized, a super luminescent diode (SLD) light source which has already been on sale can be used as the light source 1. Even when any absorption band of the above-described aqueous absorption bands is used, an arbitrary semiconductor light source to which the wavelength adapt can be utilized. Although according to the embodiment, the light having the wavelength substantially in correspondence with the wavelength of the absorption peak of glucose is used, the absorption spectrum of near infrared light of a solid or a liquid is always widened by 10 nm through several tens nm and accordingly, there can be used light having a wavelength shifted from the absorption peak by several tens nm. Further, although according to the embodiment, light having a single wavelength of the glucose a absorption band is used, by using light having a plurality of wavelengths which can be absorbed by substances other than glucose and exposing a sample under the light by switching the wavelengths of the light, concentrations of substances other than glucose can be measured substantially simultaneously. By switching the wavelength of light irradiated on a sample and monitoring a change in a concentration of a substance (interference subjects) other than glucose having absorption in a wavelength at a vicinity of a wavelength of light used in measuring glucose, the glucose concentration can also be monitored accurately regardless of a change in the concentration of the interference subjects.

Reference numerals or notations used in the drawings are summarized as follows. Numeral 1 designates a light source, numerals 2, 6 and 8 designate lenses, numeral 3 designates a beam splitter, numeral 4 designates a mirror, numeral 5 designates PZT, numeral 7 designates a sample, numeral 9 designates a photo detector, numeral 10 designates an oscillator, numeral 11 designates an amplifier, notations 12-1, 12-2, ..., 12-L designate lock-in amps, numeral 14 designates a signal processing unit, numeral 15 designates an electro-optic modulator, notations 16-1, 16-2, ..., 16-L designate frequency multipliers, notations 17-1, 17-2, ..., 17-L designate band-pass filters, notations 19-1, 19-2, ..., 19-L designate detectors, numeral 21 designates an optical coupler, numerals 22 and 23 designate collimating lenses, numeral 24 designates a stage, numeral 25 designates a linear motion stage, numeral 26 designates an analog processing circuit, numerals 30 and 31 designate wedge plates, numeral 40 designates reference light, numeral 41 designates incident light, numeral 42 designates a predetermined point in a sample, numeral 43 designates signal light, numerals 50, 51, 52 and 53 designate optical fibers, numeral 54 designates a first chassis, numeral 55 designates a display unit, numeral 56 designates a second chassis, numeral 57 designates a band, numeral 58 designates a test subject, numeral 59 designates an A-D converter, numeral 60 designates a central processing unit, numeral 61 designates a motor control circuit, numeral 62 designates the eyeball, numeral 63 designates the cornea, numeral 64 designates the retina and numeral 65 designates a collimating lens.

What is claimed is:

1. An inspection apparatus using an optical interferometer comprising splitting and combining means for splitting light from a light source into incident light irradiated on a sample and a reference light and combining signal light which is light scattered or reflected by the sample and the reference light, a modulator for subjecting any of the incident light, the reference light and the signal light to phase modulation and a photo detector for detecting light combined by the splitting and combining means, said inspection apparatus further comprising:

detecting means for separating and detecting amplitudes of first signal components having frequencies of multiples of odd numbers of a fundamental modulation frequency of the modulator and amplitudes of second signal components having frequencies of multiples of even numbers of the fundamental modulation frequency; and means for calculating an intensity of the signal light by using the amplitudes of the first and the second signal components.

2. The inspection apparatus using an optical interferometer according to claim 1:

wherein the detecting means comprises:
first detecting means for detecting the amplitudes of the first signal components; and
second detecting means for detecting the amplitudes of the second signal components.

3. The inspection apparatus using an optical interferometer according to claim 2:

wherein the first and the second inspecting means are lock-in amplifiers.

4. The inspection apparatus using an optical interferometer according to claim 2:

wherein the modulator is an electro-optic modulator, the first detecting means includes first band-pass filters for passing the first signal components and first detectors connected to the first band-pass filters and the second detecting means includes second band-pass filters for passing the second signal components and second detectors connected to the second band-pass filters.

5. The inspection apparatus using an optical interferometer according to claim 1:

wherein the detecting means calculates the amplitudes of the first and the second signal components by Fourier transformation.

6. An inspection apparatus using an optical interferometer comprising splitting and combining means for splitting light from a light source into incident light irradiated on a sample and reference light and combining signal light which is light scattered or reflected by the sample and the reference light, a modulator for subjecting the incident light and the signal light into phase modulation and a photo detector for detecting light combined by the splitting and combining means, said inspection apparatus further comprising:

first detecting means for detecting amplitudes of first signal components having frequencies of multiples of odd numbers of a fundamental modulation frequency of the modulator in a signal from the photo detector;

second detecting means for extracting and detecting amplitudes of second signal components having frequencies of multiples of even numbers of the fundamental modulation frequency in the signal from the photo detector; and means for calculating an intensity of the signal light by using the amplitudes of the first and the second signal components.

7. The inspection apparatus using an optical interferometer according to claim 6:

wherein the intensity of the signal light V* is calculated by the following equation $$V^* = \frac{1}{2}\sqrt{\frac{\sum_m V_{2m-1}^2}{\sum_m J_{2m-1}^2(\theta)} + \frac{\sum_n V_{2n}^2}{\sum_n J_{2n}^2(\theta)}}$$

where $m_{max}$ and $n_{max}$ are predetermined integers, m is an integer of $1, 2, \ldots, m_{max}$, n is an integer of $1, 2, \ldots, n_{max}$, the amplitudes of the first signal components are designates by $V_{2m-1}$, the amplitudes of the second signal components are designated by $V_{2n}$, $J_{2m-1}$ and $J_{2n}$ designate Bessel functions and $\theta$ designates an amplitude of the phase modulation provided by the modulator.

8. The inspection apparatus using an optical interferometer according to claim 6:

wherein the intensity of the signal light V* is calculated by the following equation $$V^* = \frac{1}{2}\sqrt{\frac{V_1^2}{J_1^2(\theta)} + \frac{V_2^2}{J_2^2(\theta)}}$$

where the multiple of the odd number is 1, the multiple of the even number is 2, the amplitude of the first signal component is designated by $V_1$, the amplitude of the second signal component is designated by $V_2$ and $J_1$ and $J_2$ designate Bessel function.

9. An inspection apparatus using an optical interferometer comprising splitting and combining means for splitting light from a light source into incident light irradiated on a sample and reference light and combining signal light which is light scattered or reflected by the sample and the reference light, a modulator for subjecting the incident light and the signal light into phase modulation and a photo detector for detecting light combined by the splitting and combining means, said inspection apparatus further comprising:

Fourier transforming means for subjecting a signal from the photo detector for separating and detecting amplitudes of first signal components having frequencies of multiples of odd numbers of a fundamental modulation frequency of the modulator in the signal from the photo detector and amplitudes of second signal components having frequencies of multiples of even numbers of the fundamental modulation frequency to Fourier transformation; and means for calculating an intensity of the signal light by using the amplitudes of the first and the second signal components.

10. An inspection apparatus using an optical interferometer comprising splitting and combining means for splitting light from a light source into incident light irradiated on a sample and reference light and combining signal light which is light scattered or reflected by the sample and the reference light, a modulator for subjecting the incident light and the signal light into phase modulation and a photo detector for detecting light combined by the splitting and combining means, said inspection apparatus further comprising:

detecting means for separating and detecting amplitudes of first signal components having frequencies of multiples of odd numbers of a fundamental modulation frequency of the modulator in a signal from the photo detector and amplitudes of second signal components of frequencies of multiples of even numbers of the fundamental modulation frequency; and means for calculating an intensity of the signal light by using the amplitudes of the first and the second signal components.

11. An inspection apparatus using an optical interferometer comprising splitting and combining means for splitting light from a light source into incident light irradiated on a sample and reference light and combining signal light which is light scattered or reflected by the sample and the reference light, a modulator for subjecting the incident light into phase modulation and a photo detector for detecting light combined by the splitting and combining means, said inspection apparatus further comprising:

detecting means for separating and detecting amplitudes of first signal components having frequencies of multiples of odd numbers of a fundamental modulation frequency of the modulator in a signal from the photo detector and amplitudes of second signal components of frequencies of multiples of even numbers of the fundamental modulation frequency; and means for calculating an intensity of the signal light by using the amplitudes of the first and the second signal components.

12. An inspection apparatus using an optical interferometer, said inspection apparatus comprising:

detecting means for separating and detecting amplitudes of first signal components having frequencies of multiples of odd numbers of a fundamental frequency of phase modulation provided to reference light and amplitudes of second signal components having frequencies of multiples of even numbers of the fundamental modulation frequency in an output signal from a photo detector for detecting light scattered or reflected by a sample as signal light; and means for calculating an intensity of the signal light by using the amplitudes of the first and the second signal components.

13. An inspecting method using an optical interferometer, said inspecting method comprising:

a step of splitting light from a light source into incident light irradiated on a sample and reference light, changing an optical-path length of the reference light by a predetermined frequency and forming light produced by combining signal light which is light scattered or reflected by the sample and the reference light; and a step of separating and inspecting the signal light from the combined light;

a step of separating and inspecting amplitudes of first signal components having frequencies of multiples of odd numbers of the predetermined frequency in the signal light and amplitudes of second signal components having frequencies of multiples of even numbers of the predetermined frequency; and a step of calculating an intensity of the signal light by using the amplitudes of the first and the second signal component.

14. The inspecting method using an optical interferometer according to claim 13:

wherein the intensity of the signal light $V^*$ is calculated by the following equation $$V^* = \frac{1}{2}\sqrt{\frac{\sum_m V_{2m-1}^2}{\sum_m J_{2m-1}^2(2kA)} + \frac{\sum_n V_{2n}^2}{\sum_n J_{2n}^2(2kA)}}$$

where $m_{max}$ and $n_{max}$ are predetermined integers, m is an integer of $1, 2, \ldots, m_{max}$, n is an integer of $1, 2, \ldots, n_{max}$, the amplitudes of the first signal components are designated by $V_{2m-1}$, the amplitudes of the second signal components are designated by $V_{2n}$, a wavelength of the light from the light source is designated by $\lambda$, $J_{2m-1}$ and $J_{2n}$ designate Bessel functions and 2A designates an amplitude of a change of the optical-path length and k is set as $k=2\pi/\lambda$.

15. The inspecting method using an optical interferometer according to claim 13:

wherein the intensity of the signal light $V^*$ is calculated by the following equation $$V^* = \frac{1}{2}\sqrt{\frac{V_1^2}{J_1^2(2kA)} + \frac{V_2^2}{J_2^2(2kA)}}$$

where the multiple of the odd number is 1, the multiple of the even number is 2, the amplitude of the first signal component is $V_1$, the amplitude of the second signal component is $V_2$, a wavelength of the light from the light source is designated by $\lambda$, $J_1$ and $J_2$ designate Bessel functions, 2A designates an amplitude of a change of the optical-path length and k is set as $k=2\pi/\lambda$.

16. A blood glucose level monitoring apparatus for monitoring a blood glucose level in a biomedical tissue by detecting a glucose concentration in the biomedical tissue by an inspection apparatus using an optical interferometer comprising splitting and combining means for splitting light from a light source into incident light irradiated on the biomedical tissue and reference light and combining signal light which is light scattered or reflected by the biomedical tissue and the reference light, a modulator for subjecting the signal light to phase modulation and a photo detector for detecting light combined by the splitting and combining means, said glucose monitoring apparatus comprising:

first detecting means for detecting an amplitude $V_1$ of a first signal component having a frequency of a multiple of one of a fundamental modulation frequency of the modulator;

second detecting means for separating and detecting an amplitude $V_2$ of a second signal component having a frequency of a multiple of two of the fundamental modulation frequency; and means for calculating an intensity V* of the signal light by the following equation $$V^* = \frac{1}{2}\sqrt{\frac{V_1^2}{J_1^2(\theta)} + \frac{V_2^2}{J_2^2(\theta)}}$$

where $J_1$ and $J_2$ designate Bessel functions and $\theta$ designates an amplitude of the phase modulation of the signal light, by using the amplitudes of the first and the second signal components;

wherein the glucose concentration is detected by calculating an optical-path length between a plurality of interfaces of a tissue in the biomedical tissue and attenuation of light between the plurality of interfaces.

17. A blood glucose level monitoring apparatus for monitoring a blood glucose level in a biomedical tissue by detecting a glucose concentration in the biomedical tissue by an inspection apparatus using an optical interferometer comprising splitting and combining means for splitting light from a light source into incident light irradiated on the biomedical tissue and reference light and combining signal light which is light scattered or reflected by the biomedical tissue and the reference light, a modulator for subjecting the signal light to phase modulation and a photo detector for detecting light combined by the splitting and combining means, said glucose monitoring apparatus comprising:

Fourier transforming means for subjecting to Fourier transformation, a signal from the photo detector for separating and detecting an amplitude $V_1$ of a first signal component having a frequency of a multiple of an odd number of a fundamental modulation frequency of the modulator and an amplitude $V_2$ of a second signal component having a frequency of multiple of an even number of the fundamental modulation frequency;

wherein an intensity of the signal light V* is calculated by the following equation $$V^* = \frac{1}{2}\sqrt{\frac{V_1^2}{J_1^2(\theta)} + \frac{V_2^2}{J_2^2(\theta)}}$$

where $J_1$ and $J_2$ designate Bessel functions and $\theta$ designates an amplitude of the phase modulation of the signal light, by using the amplitudes of the first and the second signal components and the glucose concentration is detected by calculating an optical-path length between a plurality of interfaces in a tissue of the biomedical tissue and attenuation of light between the plurality of interfaces.

* * * * *